United States Patent [19]

Capone

[11] Patent Number: 4,653,334
[45] Date of Patent: Mar. 31, 1987

[54] FLOW INDUCER
[75] Inventor: David M. Capone, Oakmont, Pa.
[73] Assignee: Ametek, Inc., New York, N.Y.
[21] Appl. No.: 820,002
[22] Filed: Jan. 21, 1986
[51] Int. Cl.$^4$ .............................................. G01N 1/14
[52] U.S. Cl. ................................ 73/863.81; 73/863.41
[58] Field of Search ........... 73/863.83, 863.81, 863.23, 73/864.34, 864.73, 864.81, 863.02, 863.41, 863.43, 863.03

[56] References Cited
U.S. PATENT DOCUMENTS

| | | | |
|---|---|---|---|
| 2,814,952 | 12/1957 | Ryart, Jr. et al. | 73/863.83 |
| 3,473,388 | 10/1969 | Lynn | 73/863.03 |
| 3,859,842 | 1/1975 | Bosch | 73/863.03 |
| 3,866,475 | 2/1975 | Thompson et al. | 73/863.03 |
| 4,008,620 | 2/1977 | Narato et al. | 73/864.34 |
| 4,047,437 | 9/1977 | Brooks | 73/863.81 |
| 4,118,987 | 10/1978 | Zeh | 73/863.61 |
| 4,161,883 | 7/1979 | Laird et al. | 73/863.81 |
| 4,317,379 | 3/1982 | Oberlander et al. | 73/863.83 |
| 4,561,288 | 12/1985 | Moenkhaus | 73/863.83 |

Primary Examiner—Michael J. Tokar
Assistant Examiner—Robert R. Raevis
Attorney, Agent, or Firm—Buell, Ziesenheim, Beck & Alstadt

[57] ABSTRACT

A flow inducer apparatus for positioning in a duct containing a flowing stream for continuously and rapidly receiving a sample of gas from and returning said sample to the flowing stream in said duct. Said apparatus comprises inlet opening means extending around an entire outer circumference of said apparatus to receive the sample of said flowing stream regardless of the rotational disposition of said apparatus in the duct. Said apparatus also comprises an integral discharge aspirator means. The discharge aspirator means is open to the surrounding duct along an entire outer circumference of said apparatus for receiving a portion of said flowing stream regardless of the rotational disposition of said apparatus in the duct. The discharge aspirator means is adapted so that the movement of the stream flowing in the duct tends to draw the sample through the apparatus and thereby provide the energy for operation of the flow inducer.

12 Claims, 5 Drawing Figures

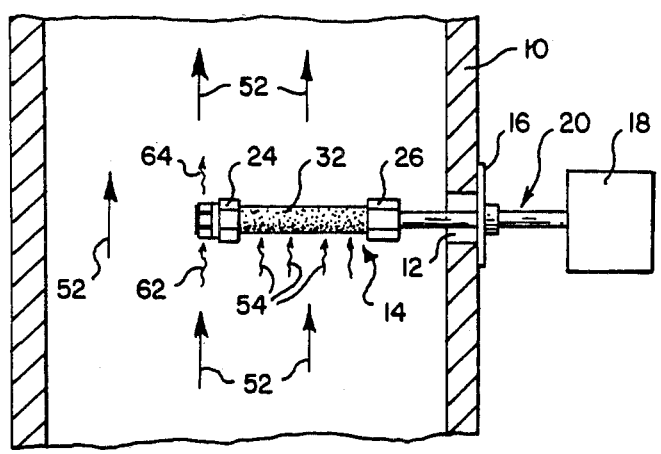
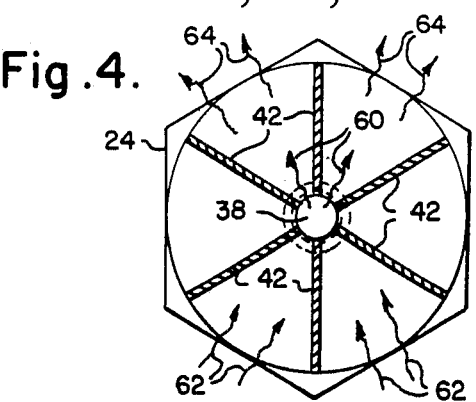
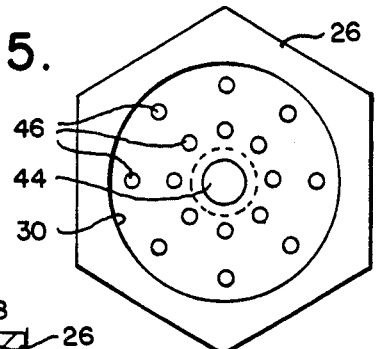
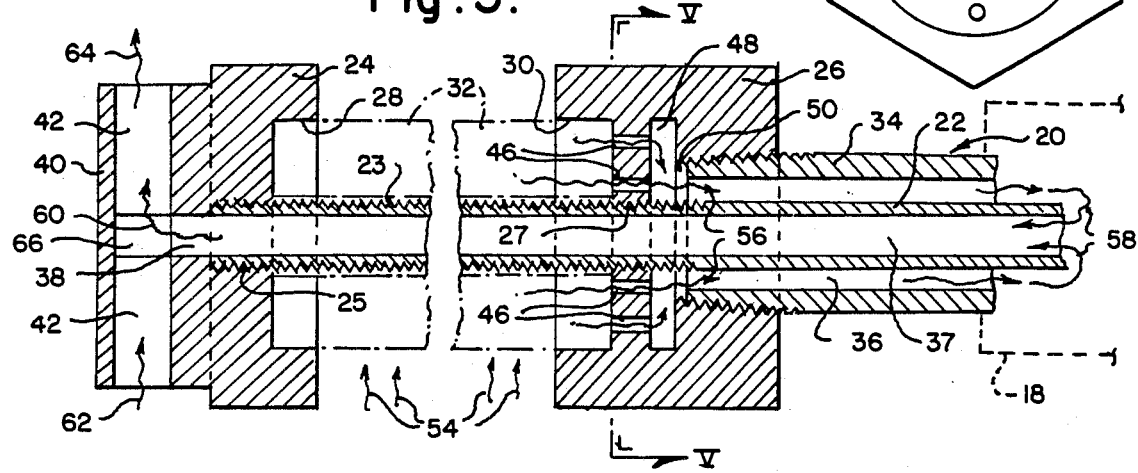
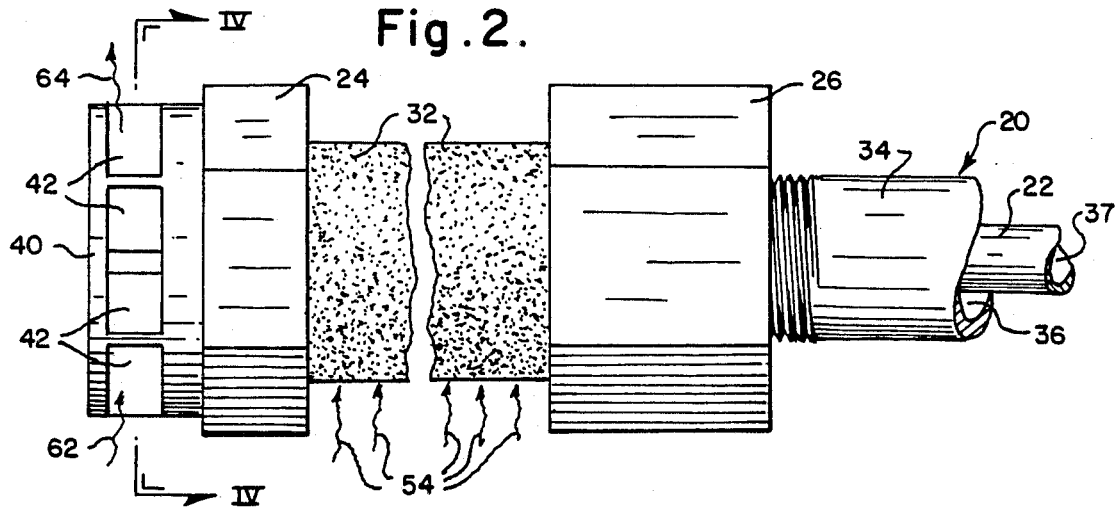

FLOW INDUCER

This invention relates to a flow inducer apparatus for rapidly and continuously extracting a gas sample from a main stream flowing in a duct and then returning said sample to the main stream. The flow inducer utilizes the energy of the main stream flowing in the duct to enhance the rapidity of extraction and return of the gas sample.

The flow inducer apparatus can be disposed in a duct through which a hot gas is flowing, such as a chimney passing hot flue gas. The longitudinal axis of the flow inducer is disposed transversely with respect to the direction of flow of the main flue gas stream. The flow inducer is adapted so that one portion of the main stream passes through the flow inducer in a direction transverse to the axis of the flow inducer at the forward end thereof and creates an aspiration effect at the forward end of the flow inducer which continuously encourages inflow of another portion of the flowing stream (the gas sample) at an intermediate region of the flow inducer. The gas sample then flows longitudinally through the flow inducer in the direction of the axis thereof. The flow inducer can be connected to a measuring instrument and the gas sample can be passed in contact with a sensing element of the measuring instrument to measure the content of a component thereof, such as oxygen. The gas sample is then returned to the flowing stream. The measuring instrument is generally outside of the duct, but can be disposed inside of the duct, if desired.

It is an advantageous feature of the flow inducer that when it is disposed so that its longitudinal axis is transverse to the flow of primary gas in a duct it is fully functional at any rotational disposition of the flow inducer in the duct. The gas sample inlet opening of the flow inducer extends around an entire circumference of the apparatus to receive a sample of the flowing stream regardless of the rotational disposition of the apparatus. The gas sample inlet opening can comprise a cylindrical porous filter element.

The discharge opening of the flow inducer lies on the longitudinal axis of the flow inducer but is disposed in cooperative association with integral aspirator means, such as a venturi, whose axis is transverse to the longitudinal axis of the flow inducer. The venturi can comprise a plurality of ribs having lateral enclosure means. The discharge opening of the flow inducer comprises a central opening at the throat of the venturi and the ribs radiate outwardly from said central opening. The outward radiation of the ribs allows a portion of the main stream flowing in the duct to pass through the ribs at a velocity which increases in its approach to the central opening and decreases in its withdrawal from the central opening. The venturi ribs are open to the flowing stream along an entire circumference of the flow inducer to receive and discharge a portion of the flowing stream and create a reduced pressure at the throat of the venturi regardless of the rotational disposition of the apparatus.

The flow inducer can comprise inner and outer elongated generally concentric conduit means defining inner passageway means and annular passageway means. Inlet opening means is provided for admitting a gas sample to said annular passageway means. Said inlet opening means is at an intermediate position along the longitudinal axis of the apparatus. The inlet opening means is open to the surroundings of the flow inducer along substantially an entire circumference of the flow inducer. Flow reversal passageway means is disposed rearwardly in the apparatus with respect to said opening means for connecting the annular passageway means and the inner passageway means. The sensing element of a measuring instrument can be disposed in the region of the flow reversal passageway means so that the sample stream comes into contact with said sensing element.

Discharge opening means coaxial with respect to said inner passageway means is disposed forwardly in the apparatus with respect to said inlet opening means for discharging a flowing stream from said inner passageway means. A plurality of ribs are disposed forwardly of the discharge opening means. The ribs radiate outwardly from the discharge opening means and outwardly from the longitudinal axis of the flow inducer. Lateral rib enclosure means are provided for laterally enclosing the ribs and defining a plurality of tapered passageway means lying on a plane transverse to the longitudinal axis of the flow inducer. The tapered passageway means is open to the discharge opening means near the narrowest portion thereof and open to the surroundings near the widest portion thereof. The widest portion of the tapered passageway means is open to the surroundings along substantially an entire outer circumference of the apparatus. Thereby, the radial ribs form a venturi providing a reduced pressure adjacent the discharge opening means, which is at the throat of the venturi.

The portion of the flowing stream passing through the venturi thereby creates an aspiration effect near the discharge opening means. This aspirating effect tends to draw the gas sample into the inlet opening means and through the apparatus. It is seen that the apparatus is adapted so that one portion of the primary stream provides the energy for circulating another portion of the primary stream through the apparatus in a continuous and rapid manner regardless of the rotational positioning of the device in the primary stream.

This invention will be more clearly understood by reference to the drawings in which:

FIG. 1 shows the flow inducer mounted on the wall of a chimney,

FIG. 2 presents an exterior view of a forward fragment of the flow inducer,

FIG. 3 presents a cross-sectional view of a forward fragment of the flow inducer, FIG. 4 is a view through section IV—IV of FIG. 2, and FIG. 5 is a view through section V—V of FIG. 3.

FIG. 1 shows chimney stack 10 having side opening 12 through which is inserted an elongated flow inducer of this invention, indicated generally at 14. Flow inducer 14 is mounted on chimney 10 by means of a bracket 16 and is connected to any conventional measuring instrument 18 outside of chimney 10 for measuring oxygen or other gaseous component of the flue gas. A conduit assembly 20 extends through the wall of chimney 10 for connection with measuring instrument 18. Measuring instrument 18 is conveniently disposed outside of the environment of hot flue gas.

FIGS. 2 and 3 show that conduit assembly 20 includes essentially concentric conduits 22 and 34. Central conduit 22 is exteriorly threaded at 23 and serves as a support for mounting front member 24 which is interiorly threaded at 25 and rear member 26 which is interiorly threaded at 27. Front member 24 is provided with an indentation 28 for receiving the front end of non-threaded porous air filter element 32 and rear member 26 is provided with an indentation 30 for receiving the rear end of air filter element 32. Exterior conduit 34 is threadedly connected within recess 50 of rear member 26 so that annular or outer space 36 is formed between exterior conduit 34 and interior conduit 22. Annular space 36 discharges into measuring instrument 18, schematically indicated in FIG. 3, allowing the sample stream to contact a sensing device, not shown. Return central passageway 37 of conduit 22 is open to instrument 18 for removing the sample stream from instrument 18.

FIGS. 3 and 4 show that front member 24 has a discharge opening 38. Solid plate 40 is secured to and spaced apart from front member 24 by means of a plurality of radially extending ribs 42. Radial ribs 42 extend outwardly from central opening 38 and from the longitudinal axis of the flow inducer to form tapered passageways between ribs 42. As shown in FIG. 4, the tapered passageways are the most narrow near discharge opening 38 and are the widest near the outer circumference of the apparatus.

FIG. 5 shows that rear member 26 is provided with central opening 44 and a plurality of eccentric openings 46. As shown in FIG. 3, eccentric openings 46 extend through rear member 26 to a chamber 48 which is open through recess 50 to annular space 36.

The operation of the apparatus will now be explained. As shown in FIG. 1, flow inducer 14 is disposed in chimney 10 with its longitudinal axis transverse to the flow of the main stream of flue gas indicated by arrows 52. A sample of the flue gas, as indicated by arrows 54, enters the flow inducer through tubular air filter element 32. The filter element removes soot particles from the gas sample. The sample gas flow within air filter 32 is indicated by arrows 56 which indicate flow through eccentric openings 46 to chamber 48 and then into annular space 36. The flow stream continues from annular space 36 into measuring instrument 18 followed by return to the flow inducer through passageway 37 of interior conduit 22, as indicated schematically by U-turn arrows 58 in FIG. 3.

The sample stream exits from passageway 37 of interior conduit 22 through central opening 38, as indicated by arrow 60 FIG. 3. The flow through opening 38 at arrow 60 is assisted by an aspiration effect created by stream 62 which is directed by ribs 42 past opening 38. See FIGS. 3 and 4. The tapered passageways provided by ribs 42 below and above discharge opening 38 provides a venturi effect for stream 62 creating a reduced pressure at discharge opening 38. The reduced pressure draws stream 60 into stream 62 so that a combined stream 64 discharges from the outwardly tapered passageways formed by ribs 42.

Reference to FIG. 4 shows that the symmetrical radial arrangement of ribs 42 allows complete freedom of rotational positioning of flow inducer 14 in chimney 10. Regardless of the rotational positioning of flow inducer 14, the flow of flue gas indicated by arrows 62 is funneled past central discharge opening 38 to create a venturi effect at discharge opening 38, inducing a reduced pressure at zone 66 outside of opening 38. The reduced pressure tends to draw stream 60 from opening 38 allowing it to be mixed with stream 62 and be discharged as combined stream 64. Similarly, the tubular configuration of porous filter element 32 permits incoming gas sample 54 to be received regardless of the rotational positioning of flow inducer 14.

The reduced pressure effect created by the plurality of generally symmetrically disposed radial ribs 42 tends to increase the rate of circulation of sample stream 54 through the flow inducer and past the sensing element in measuring instrument 18. Thereby, the ribbed assembly induces continuous and rapid lateral flow of sample stream 54 to instrument 18, which can conveniently be located outside of chimney 10, followed by return of the sample gas from instrument 18 by lateral flow. Thereby, there is a continuous and rapid change of the flue gas sample at the sensing element of the measuring instrument even though the sensing element is outside of the flow path of primary flue gas stream 52. Furthermore, the energy content of one portion of the main stream (62) is utilized to motivate flow of another portion of the main stream (54) through the flow inducer.

I claim:

1. A flow inducer apparatus for receiving a sample of a flowing stream in a duct comprising inlet opening means in said apparatus for receiving said sample into said apparatus, said inlet opening means being open to said flowing stream along substantially an entire circumference of said apparatus to receive said sample regardless of the rotational disposition of said apparatus in said duct, aspirator means in said apparatus for aspirating said sample into said inlet opening means and through said apparatus, said aspirator means being open to the flowing stream along substantially an entire circumference of said apparatus to receive an aspirating portion of said flowing stream to accomplish said aspiration regardless of the rotational disposition of said apparatus in said duct.

2. The flow inducer apparatus of claim 1 wherein said inlet opening means comprises a tubular porous filter element.

3. The flow inducer apparatus of claim 1 wherein said aspirator means comprises a venturi.

4. The flow inducer apparatus of claim 1 wherein said aspirator means comprises a plurality of enclosed ribs extending radially outwardly from sample discharge opening means in said apparatus.

5. The flow inducer apparatus of claim 1 wherein said aspirator means is at one end of said apparatus and said inlet opening means is at an intermediate position in said apparatus.

6. A flow inducer apparatus whose surroundings comprise a flowing stream comprising inner and outer generally concentric conduit means defining inner passageway means and annular passageway means, inlet opening means for admitting a flowing stream to said annular passageway means, said inlet opening means being open to the surroundings around substantially an entire outer circumference of said apparatus, flow reversal passageway means in said apparatus for connecting said annular passageway means and said inner passageway means, discharge opening means in said inner passageway means for discharging a flowing stream from said inner passageway means, a plurality of ribs disposed around said discharge opening means and radiating outwardly therefrom, rib enclosure means for laterally enclosing said ribs, said ribs defining a plurality of tapered passageway means extending transversely of the axis of said discharge opening means, said tapered passageway means being open to said discharge opening means near the center thereof and open to the surroundings around substantially an entire outer circumference of said apparatus.

7. The flow inducer apparatus of claim 6 wherein said inlet opening means is disposed at an intermediate position with respect to said flow reversal passageway means and said discharge opening means.

8. The flow inducer apparatus of claim 6 wherein said inlet opening means comprises a tubular porous filter element.

9. The flow inducer apparatus of claim 6 including sensing means of a measuring instrument in the region of said flow reversal passageway means.

10. The flow inducer apparatus of claim 6 including oxygen gas sensing means of a measuring instrument for measuring oxygen content of said flowing stream, said sensing means being in the region of said flow reversal passageway means.

11. The flow inducer apparatus of claim 6 mounted on the wall of a chimney and disposed transversely to the direction of flow of flue gas in said chimney.

12. A flow inducer apparatus in combination with a duct containing a flowing stream, said apparatus comprising inner and outer generally concentric conduit means defining inner passageway means and annular passageway means, inlet opening means for admitting a flowing stream to said annular passageway means, said inlet opening means being open to the interior of said duct along substantially an entire circumference of said apparatus, flow reversal passageway means disposed rearwardly in said apparatus for connecting said annular passageway means and said inner passageway means, discharge opening means disposed forwardly in said apparatus with respect to said inlet opening means for discharging a flowing stream from said inner passageway means, a plurality of ribs disposed forwardly with respect to said discharge opening means and extending radially outwardly therefrom, rib enclosure means for laterally enclosing said ribs and defining a plurality of tapered passageway means extending transversely of the longitudinal axis of said concentric conduit means, said tapered passageway means being open to said discharge opening means near the center thereof, and said tapered passageway means being open to said duct along substantially an entire outer circumference of said apparatus.

* * * * *